(12) United States Patent
Horan et al.

(10) Patent No.: US 8,057,507 B2
(45) Date of Patent: Nov. 15, 2011

(54) VASCULAR FILTER

(75) Inventors: Steven Horan, Knocknacarra (IE); Jacquline O'Gorman, Cratloe (IE); Aidan Goggin, Athenry (IE)

(73) Assignee: Novate Medical Limited, Dublin (IE)

( * ) Notice: Subject to any disclaimer, the term of this patent is extended or adjusted under 35 U.S.C. 154(b) by 163 days.

(21) Appl. No.: 12/355,556

(22) Filed: Jan. 16, 2009

(65) Prior Publication Data

US 2010/0185227 A1    Jul. 22, 2010

(51) Int. Cl.
     *A61F 2/01*      (2006.01)
(52) U.S. Cl. .................................................. 606/200
(58) Field of Classification Search ............ 606/108, 606/191, 194, 200, 113, 114, 127, 128, 159; 623/1.11, 1.15, 1.16, 1.24–1.26, 23.72, 2.17–2.19
See application file for complete search history.

(56) References Cited

U.S. PATENT DOCUMENTS

| | | |
|---|---|---|
| 5,344,427 A | 9/1994 | Cottenceau et al. |
| 5,375,612 A | 12/1994 | Cottenceau et al. |
| 5,383,887 A | 1/1995 | Nadal |
| 5,634,942 A | 6/1997 | Chevillon et al. |
| 5,725,550 A | 3/1998 | Nadal |
| 5,800,525 A | 9/1998 | Bachinski et al. |
| 5,853,420 A | 12/1998 | Chevillon et al. |
| 5,968,071 A | 10/1999 | Chevillon et al. |
| 6,193,739 B1 | 2/2001 | Chevillon et al. |
| 6,214,025 B1 | 4/2001 | Thistle et al. |
| 6,241,746 B1 | 6/2001 | Bosma et al. |
| 6,248,128 B1 | 6/2001 | Berry et al. |
| 6,267,776 B1 | 7/2001 | O'Connell |
| 6,312,461 B1 | 11/2001 | Unsworth et al. |
| 6,391,045 B1 * | 5/2002 | Kim et al. ..................... 606/200 |
| 6,482,227 B1 | 11/2002 | Solovay |
| 6,517,559 B1 | 2/2003 | O'Connell |
| 6,527,962 B1 | 3/2003 | Nadal |
| 6,582,447 B1 | 6/2003 | Patel et al. |
| 6,605,111 B2 | 8/2003 | Bose et al. |
| 6,635,083 B1 * | 10/2003 | Cheng et al. ................ 623/1.15 |
| 6,652,558 B2 | 11/2003 | Patel et al. |

(Continued)

FOREIGN PATENT DOCUMENTS

DE      40 30 998 A1      4/1991

(Continued)

OTHER PUBLICATIONS

European Search Report for EP 10 39 4001 mailed on Apr. 27, 2010.

(Continued)

*Primary Examiner* — Kathleen Sonnett
(74) *Attorney, Agent, or Firm* — Finnegan, Henderson, Farabow, Garrett & Dunner, LLP

(57) ABSTRACT

A vascular filter includes a proximal support hoop, a plurality of support struts, and a plurality of capture arms. The proximal support hoop extends around the internal wall of the inferior vena cava in a wave pattern having six distal peaks and six proximal peaks. The proximal support hoop includes an enlarged end element at each peak. The support struts extend longitudinally along the internal wall of the inferior vena cava in a curve. Two capture arms are connected to the proximal support hoop at each distal peak. Each capture arm extends from the distal peak to an apex in a curve. The concave portion of the first curve faces inwardly towards the concave portion of the second curve.

24 Claims, 7 Drawing Sheets

U.S. PATENT DOCUMENTS

| | | |
|---|---|---|
| 6,666,882 B1 | 12/2003 | Bose et al. |
| 6,669,721 B1 | 12/2003 | Bose et al. |
| 6,852,076 B2 | 2/2005 | Nikolic et al. |
| 6,881,218 B2 * | 4/2005 | Beyer et al. ............ 606/200 |
| 6,932,832 B2 | 8/2005 | Patel et al. |
| 6,966,923 B2 | 11/2005 | Gittings |
| 6,972,025 B2 | 12/2005 | WasDyke |
| 7,001,424 B2 | 2/2006 | Patel et al. |
| 7,094,248 B2 | 8/2006 | Bachinski et al. |
| 7,261,731 B2 | 8/2007 | Patel et al. |
| 7,279,007 B2 | 10/2007 | Nikolic et al. |
| 7,534,251 B2 | 5/2009 | WasDyke |
| 2001/0044652 A1 | 11/2001 | Moore |
| 2003/0120303 A1 | 6/2003 | Boyle et al. |
| 2003/0176888 A1 | 9/2003 | O'Connell |
| 2003/0208227 A1 | 11/2003 | Thomas |
| 2004/0019374 A1 | 1/2004 | Hojeibane et al. |
| 2004/0186550 A1 * | 9/2004 | Bonsignore ............ 623/1.15 |
| 2004/0220611 A1 | 11/2004 | Ogle |
| 2005/0096735 A1 | 5/2005 | Hojeibane et al. |
| 2005/0107822 A1 | 5/2005 | WasDyke |
| 2005/0222604 A1 | 10/2005 | Schaeffer |
| 2005/0234504 A1 | 10/2005 | WasDyke |
| 2006/0025852 A1 | 2/2006 | Armstrong et al. |
| 2007/0032816 A1 | 2/2007 | O'Connell et al. |
| 2007/0112372 A1 | 5/2007 | Sosnowski et al. |
| 2007/0203571 A1 | 8/2007 | Kaplan et al. |
| 2008/0027481 A1 | 1/2008 | Gilson et al. |
| 2008/0188887 A1 | 8/2008 | Batiste |
| 2008/0208245 A1 | 8/2008 | Hoffman |
| 2010/0185229 A1 | 7/2010 | Horan et al. |
| 2010/0185230 A1 | 7/2010 | Horan et al. |

FOREIGN PATENT DOCUMENTS

| | | |
|---|---|---|
| DE | 102008031299 A1 | 1/2010 |
| EP | 0 565 395 A1 | 10/1993 |
| EP | 0 582 493 A1 | 2/1994 |
| EP | 0 598 635 A1 | 5/1994 |
| EP | 0 605 276 A1 | 7/1994 |
| EP | 0 655 228 A1 | 5/1995 |
| EP | 0 678 284 A1 | 10/1995 |
| EP | 0678284 A1 | 10/1995 |
| EP | 0 737 451 A1 | 10/1996 |
| EP | 0 759 287 A1 | 2/1997 |
| EP | 0 582 493 A1 | 7/1997 |
| EP | 0 935 975 A1 | 8/1999 |
| EP | 0 605 276 A1 | 2/2000 |
| EP | 1 103 233 A1 | 5/2001 |
| EP | 1 258 228 A1 | 11/2002 |
| EP | 0 759 287 A1 | 2/2003 |
| EP | 0 737 451 A1 | 9/2003 |
| EP | 1 616 530 A1 | 1/2006 |
| FR | 2 718 950 | 10/1995 |
| FR | 2 718 950 A1 | 10/1995 |
| FR | 2 764 503 | 12/1998 |
| FR | 2 764 503 A1 | 12/1998 |
| FR | 2 814 670 | 4/2002 |
| FR | 2 814 670 A1 | 4/2002 |
| WO | WO 00/56390 | 9/2000 |
| WO | WO 00/66031 | 11/2000 |
| WO | WO 01/62184 A2 | 8/2001 |
| WO | WO 02/22048 A2 | 3/2002 |
| WO | WO 2006/020425 A1 | 2/2006 |
| WO | WO 2006/074163 A2 | 7/2006 |
| WO | WO 2006/107939 A1 | 10/2006 |
| WO | WO 2006/116636 A1 | 11/2006 |
| WO | WO 2008/010197 A2 | 1/2008 |

OTHER PUBLICATIONS

U.S. Appl. No. 12/688,173, filed Jan. 15, 2010 (72 pages).

* cited by examiner

US 8,057,507 B2

VASCULAR FILTER

INTRODUCTION

This invention relates to a vascular filter.

STATEMENTS OF INVENTION

According to the invention there is provided a vascular filter comprising:
one or more capture members for capturing thrombus passing through a blood vessel, and
one or more support members for supporting the one or more capture members relative to a wall of the blood vessel.

By capturing the thrombus, the filter prevents the thrombus from passing to the heart or lungs, which may cause pulmonary embolism. By supporting the capture members this ensures that the capture members are maintained in the desired location in the blood vessel.

In one embodiment of the invention the capture member is movable from a capturing configuration to an open configuration, in the capturing configuration the capture member being configured to capture thrombus passing through a blood vessel, in the open configuration the capture member being configured to facilitate unrestricted blood flow. Preferably in the capturing configuration the capture member extends towards an apex. Ideally in the capturing configuration the capture member extends towards the apex in a curve.

In another embodiment the support member is movable between a delivery configuration and a deployed configuration.

In one case at least part of the support member is configured to extend circumferentially around a wall of a blood vessel in a wave pattern. Preferably the support member comprises a plurality of connector elements, each connector element connecting a peak of the wave pattern to an adjacent peak of the wave pattern. Ideally the support member comprises an enlarged end element at a peak of the wave pattern. This arrangement results in greater flexibility, in lower strains, and in greater resistance to buckling. Most preferably in the delivery configuration the diameter of curvature of the end element is greater than the distance between adjacent connector elements. The wave pattern of the support member may comprise less than twelve distal peaks. This arrangement results in greater resistance to buckling. Preferably the wave pattern of the support member comprises less than ten distal peaks. Ideally the wave pattern of the support member comprises less than eight distal peaks. The capture member may be connected to the support member at a distal peak of the wave pattern. Preferably a first capture member is connected to the support member at a first distal peak of the wave pattern, and a second capture member is connected to the support member at the first distal peak of the wave pattern. Ideally in the capturing configuration the first capture member extends from the first distal peak of the wave pattern towards the apex in a first curve, and the second capture member extends from the first distal peak of the wave pattern towards the apex in a second curve, the concave portion of the first curve facing inwardly towards the concave portion of the second curve. This arrangement minimises any gap between adjacent capture members, and thus improves filter efficiency.

In another case at least part of the support member is configured to extend longitudinally along a wall of a blood vessel. Preferably the support member is configured to extend longitudinally in a curve. This arrangement minimises any bowing or lift-off of the support member from the wall of the blood vessel. Thus the contact force between the support member and the blood vessel is maximised which enhances resistance to buckling. Most preferably when the filter is deployed externally of a blood vessel, in the open configuration the convex portion of the curve faces radially outwardly. In the open configuration the ratio of R1:R2 may be in the range of from 1:1 to 1.5:1, where
R1 is the distance of the support member from the central longitudinal axis of the filter at the point along the support member where this distance is at a maximum, and
R2 is the distance of the support member from the central longitudinal axis of the filter at an end of the support member.

In the capturing configuration the maximum distance between the support member and a wall of a blood vessel may be less than 4 mm. In the capturing configuration the maximum distance between the support member and a wall of a blood vessel may be less than 2 mm.

In one embodiment the radial dimension of the support member is greater than 0.20 mm. This arrangement results in greater resistance to buckling. Preferably the radial dimension of the support member is greater than 0.25 mm. Ideally the radial dimension of the support member is greater than 0.30 mm.

In another embodiment at least part of the support member comprises one or more elongate elements, the width of at least one of the elongate elements being greater than 0.25 mm. This arrangement results in greater resistance to buckling. Preferably the width of the elongate element is greater than 0.30 mm. Ideally the width of the elongate element is greater than 0.35 mm.

BRIEF DESCRIPTION OF THE DRAWINGS

The invention will be more clearly understood from the following description of an embodiment thereof, given by way of example only, with reference to the accompanying drawings, in which.

DETAILED DESCRIPTION

Figure 1:
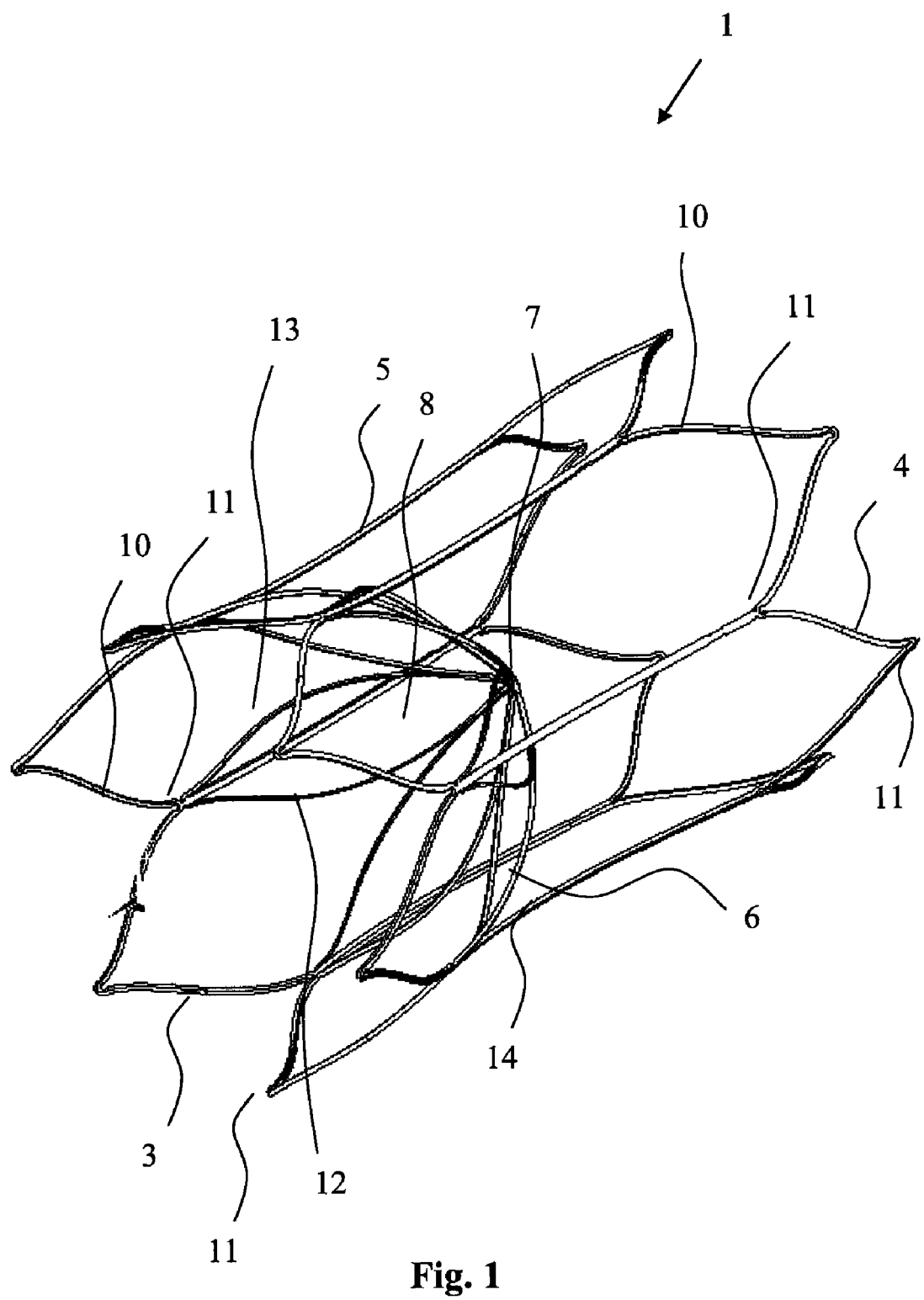
FIG. 1 is an isometric view of a vascular filter according to the invention in a deployed capturing configuration.

Referring to the drawings there is illustrated a vascular filter 1 according to the invention. The vascular filter 1 is suitable for use as an inferior vena cava filter in the inferior vena cava. The filter 1 is movable from a capturing configuration (FIG. 4) to an open configuration (FIG. 8) upon elapse of a predetermined period of time. In the capturing configuration the filter 1 is configured to capture thrombus passing through the inferior vena cava towards the heart and the lungs. The filter 1 may thus be used to prevent pulmonary embolism. In the open configuration the filter 1 is configured to facilitate unrestricted blood flow.

Figure 2:
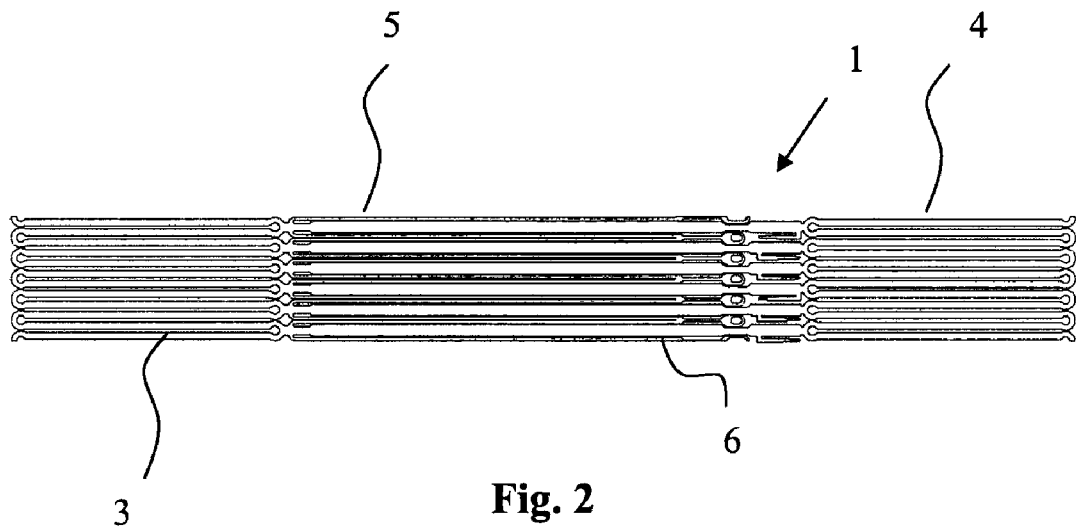
FIG. 2 is a developed side view of the vascular filter of FIG. 1 in a delivery configuration.
Figure 3:
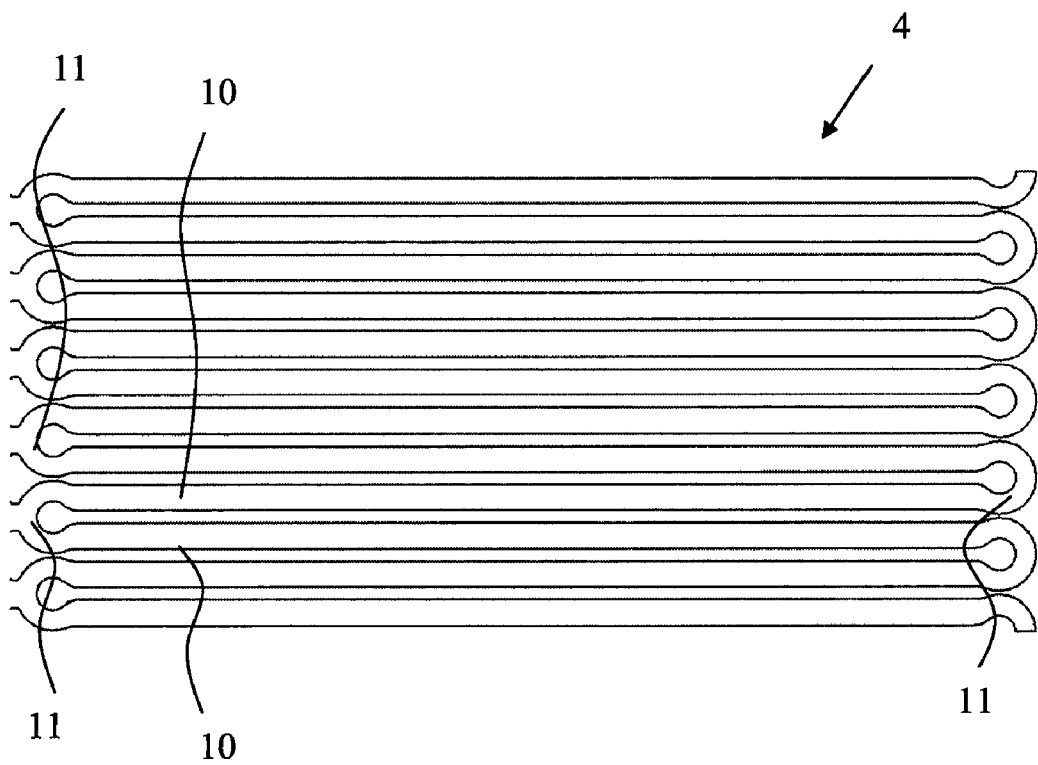
FIG. 3 is an enlarged developed side view of part of the vascular filter of FIG. 2 in the delivery configuration.
Figure 4:
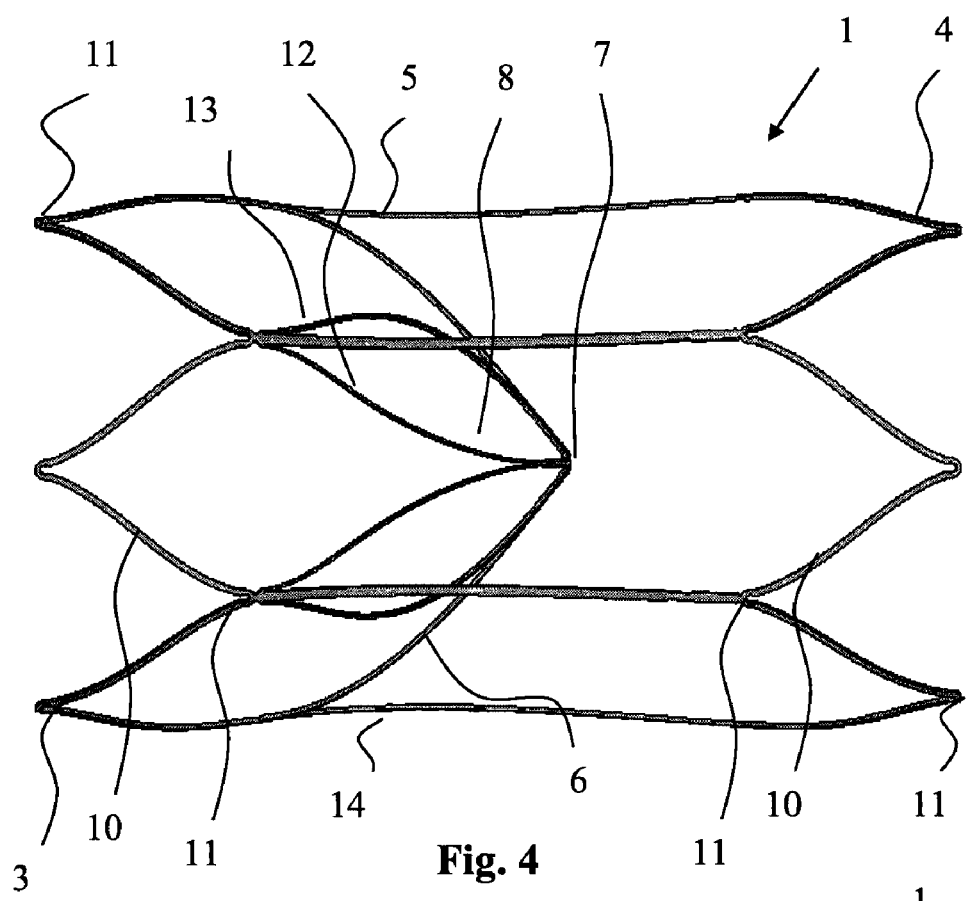
FIG. 4 is a side view of the vascular filter of FIG. 1 in the deployed capturing configuration.

The filter 1 is movable between a collapsed delivery configuration (FIGS. 2 and 3) and an expanded deployed configuration (FIGS. 1 and 4). The filter 1 is biased radially outwardly towards the deployed configuration.

As illustrated in FIG. 1, the filter 1 comprises a proximal support hoop 3 at the proximal end of the filter 1, a distal support hoop 4 at the distal end of the filter 1, and a plurality of support struts 5 extending between the proximal support hoop 3 and the distal support hoop 4.

In this patent specification, the term 'proximal' will be understood to mean the end closest to a user when carrying out a procedure accessed from a femoral vein, or the caudal end. Similarly the term 'distal' will be understood to mean the end furthest from a user when carrying out a procedure accessed from a femoral vein, or the cranial end.

Figure 5:
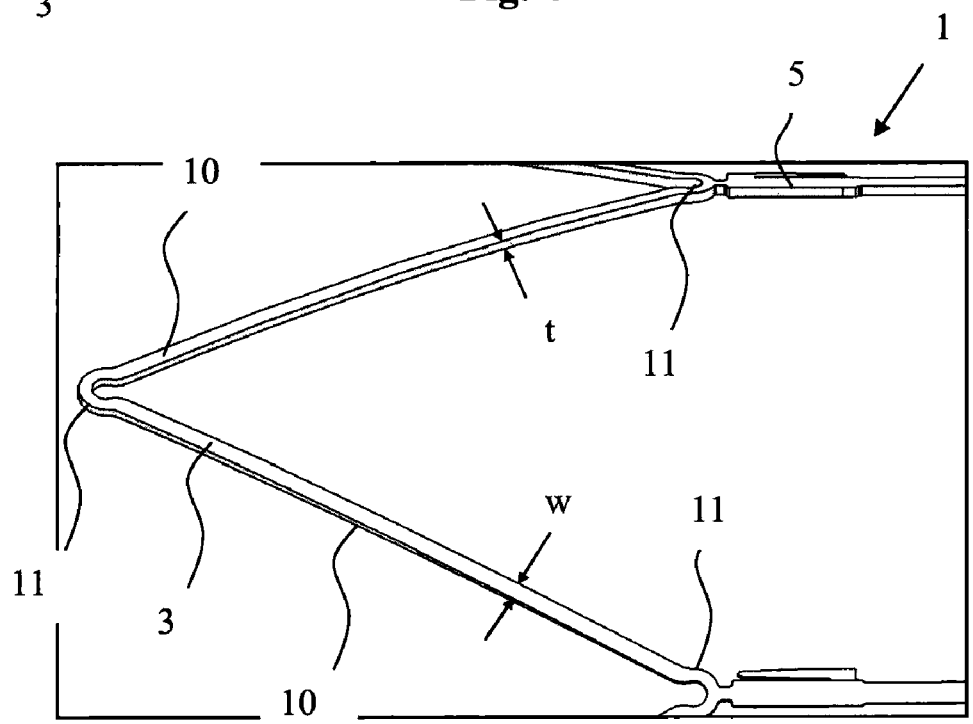
FIG. 5 is an enlarged side view of part of the vascular filter of FIG. 4 in the deployed capturing configuration.
Figure 6:
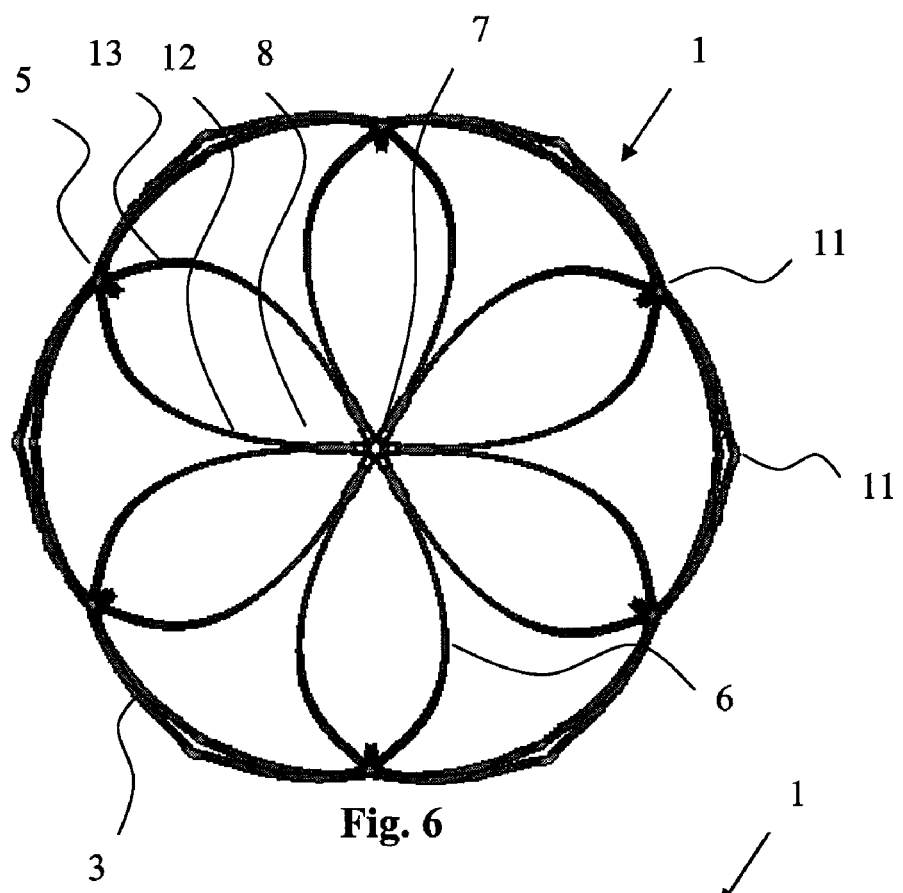
FIG. 6 is an end view of the vascular filter of FIG. 1 in the deployed capturing configuration.

The proximal support hoop 3 extends circumferentially around the internal wall of the inferior vena cava in a zig-zag wave pattern. As illustrated in FIG. 5, the proximal support hoop 3 comprises a plurality of elongate connector elements 10. Each connector element 10 connects a peak 11 of the wave pattern to an adjacent peak 11 of the wave pattern.

In this case the wave pattern of the proximal support hoop 3 comprises six distal peaks 11 and six proximal peaks 11. It has been found that the filter 1 having six distal peaks 11 and six proximal peaks 11 is particularly resistant to buckling.

The proximal support hoop 3 comprises an enlarged end element at each peak 11 of the wave pattern. In the delivery configuration, the diameter of curvature of the end element at peak 11 is greater than the distance between adjacent connector elements 10. The geometry of the peaks 11 allows for less rigid movement of the proximal support hoop 3 and also allows for lower strains in the proximal support hoop 3. Enhanced flexibility of the crown 3 minimises the probability of buckling. The proximal support hoop 3 of the filter 1 offers increased torsional flexibility. This flexibility helps to minimise the probability of buckling.

As illustrated in FIG. 5, the radial dimension or wall thickness t of the proximal support hoop 3 is 0.33 mm in this case. It has been found that the filter 1 has a greater resistance to buckling and a higher radial force. The width w of each connector element 10 is 0.38 mm in this case. The filter 1 with six distal peaks 11 and six proximal peaks 11 has a particularly low profile in the delivery configuration. This low profile enables larger strut thickness t and width w for a given delivery profile.

Similarly the distal support hoop 4 extends circumferentially around the internal wall of the inferior vena cava in a zig-zag wave pattern. The distal support hoop 4 comprises a plurality of elongate connector elements 10. Each connector element 10 connects a peak 11 of the wave pattern to an adjacent peak 11 of the wave pattern.

In this case the wave pattern of the distal support hoop 4 comprises six distal peaks 11 and six proximal peaks 11.

The distal support hoop 4 comprises an enlarged end element at each peak 11 of the wave pattern. As illustrated in FIG. 3, in the delivery configuration, the diameter of curvature of the end element at peak 11 is greater than the distance between adjacent connector elements 10.

The radial dimension or wall thickness of the distal support hoop 4 is 0.33 mm in this case. The width of each connector element 10 is 0.38 mm in this case.

The support struts 5 extend longitudinally along the internal wall of the inferior vena cava in a curve 14. The support struts 5 connect the proximal support hoop 3 to the distal support hoop 4. In this case the proximal support hoop 3, the distal support hoop 4 and the support struts 5 are formed integrally. The proximal support hoop 3, the distal support hoop 4 and the support struts 5 may be of a shape-memory material, such as Nitinol.

The radial dimension or wall thickness of each support strut 5 is 0.33 mm in this case. The width of each support strut 5 is 0.38 mm in this case.

As illustrated in FIG. 1, the filter 1 comprises twelve capture arms 6 for capturing thrombus passing through the inferior vena cava.

Each capture arm 6 is formed integrally with the proximal support hoop 3. As illustrated in FIG. 4, for each distal peak 11 of the wave pattern a first capture arm 6 is connected to the proximal support hoop 3 at the distal peak 11, and a second capture arm 6 is connected to the proximal support hoop 3 at the distal peak 11.

Each capture arm 6 is movable from the capturing configuration (FIG. 4) to the open configuration (FIG. 8) upon elapse of the predetermined period of time. In the capturing configuration the capture arms 6 are configured to capture thrombus passing through the inferior vena cava towards the heart and the lungs. In the open configuration the capture arms 6 are configured to facilitate unrestricted blood flow.

In the capturing configuration each capture arm 6 extends to an apex 7 in a curve. As illustrated in FIG. 4, for each distal peak 11 of the wave pattern, the first capture arm 6 extends from the distal peak 11 to the apex 7 in a first curve 12, and the second capture arm 6 extends from the distal peak 11 to the apex 7 in a second curve 13. The concave portion of the first curve 12 faces inwardly towards the concave portion of the second curve 13. In this manner the capture arms 6 define a generally conically shaped capture region or filtration cone 8 within which thrombus may be captured. Any gaps between adjacent capture arms 6 in the filtration cone 8 are minimised. The capture arms 6 are shape set to maximise filter efficiency.

In this specification, the term curve will be understood to mean a smooth curve or two or more discreet straight sections. For example, the capture arm 6 curvature may be heat set to extend towards the apex in a series of two straights. It is appreciated that 2 or more discrete straights, or, a smooth curve, or, a set of smooth curves, may be employed to maximise filter efficiency.

Figure 8:
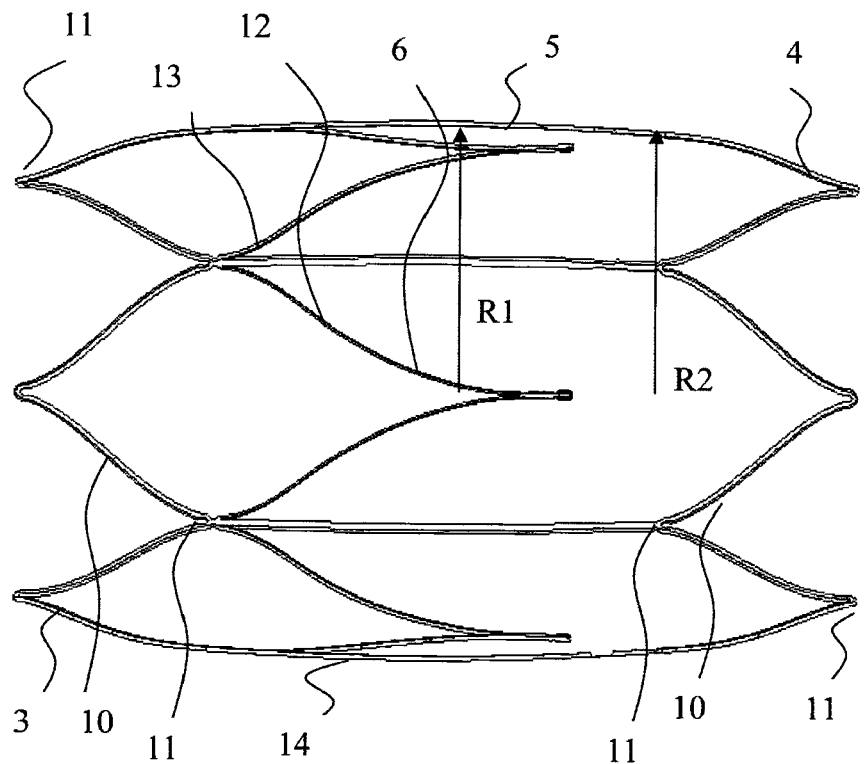
FIG. 8 is a side view of the vascular filter of FIG. 1 in a deployed open configuration.

A perimeter route is defined from a first distal peak 11 of the proximal support hoop 3 along a first connector element 10 to a proximal peak 11 of the proximal support hoop 3, from the proximal peak 11 along a second connector element 10 to a second distal peak 11 of the proximal support hoop 3, from the second distal peak 11 along a first support strut 5 to a first proximal peak 11 of the distal support hoop 4, from the first proximal peak 11 along a third connector element 10 to a distal peak 11 of the distal support hoop 4, from the distal peak 11 along a fourth connector element 10 to a second proximal peak 11 of the distal support hoop 4, from the second proximal peak 11 along a second support strut 5 to the first distal peak 11 of the proximal support hoop 3. A cell is defined within the perimeter route. The filter 1 comprises six such cells. Two capture arms 6 are attached to each cell in both the capturing configuration (FIG. 4) and the open configuration (FIG. 8). This arrangement results in a balanced cell spacing for consistent filtration pore size.

Figure 7:
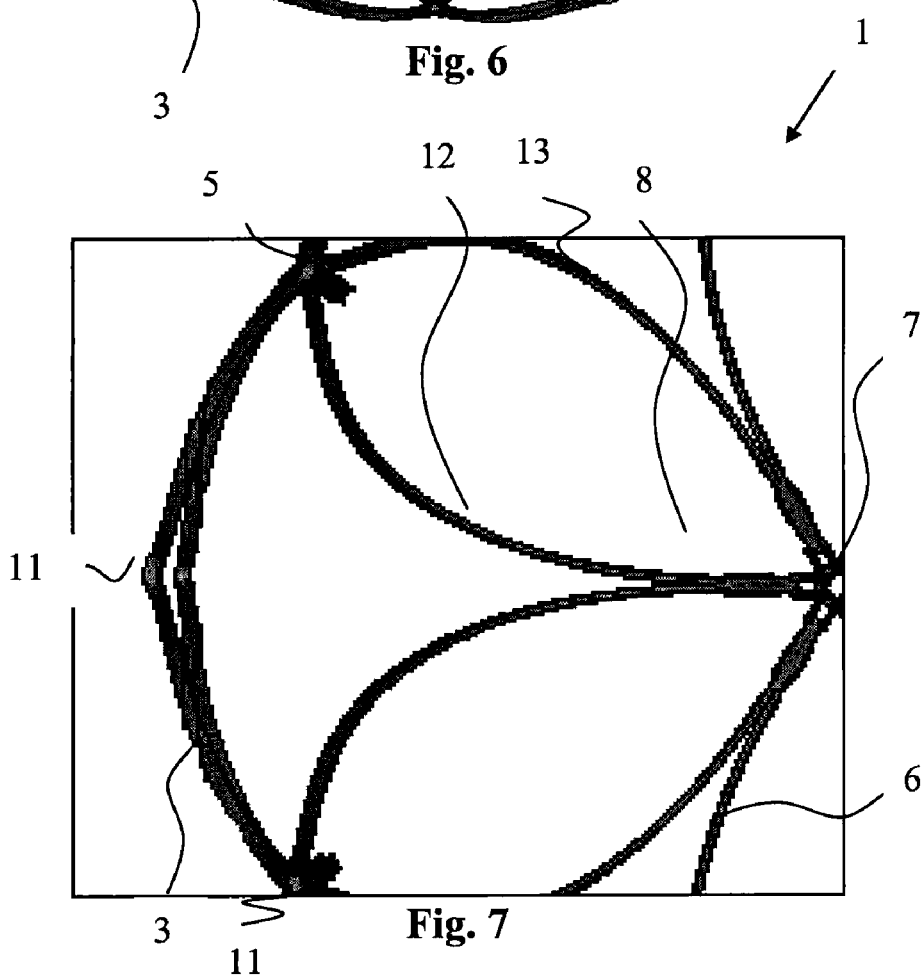
FIG. 7 is an enlarged end view of part of the vascular filter of FIG. 6 in the deployed capturing configuration.
Figure 7A:
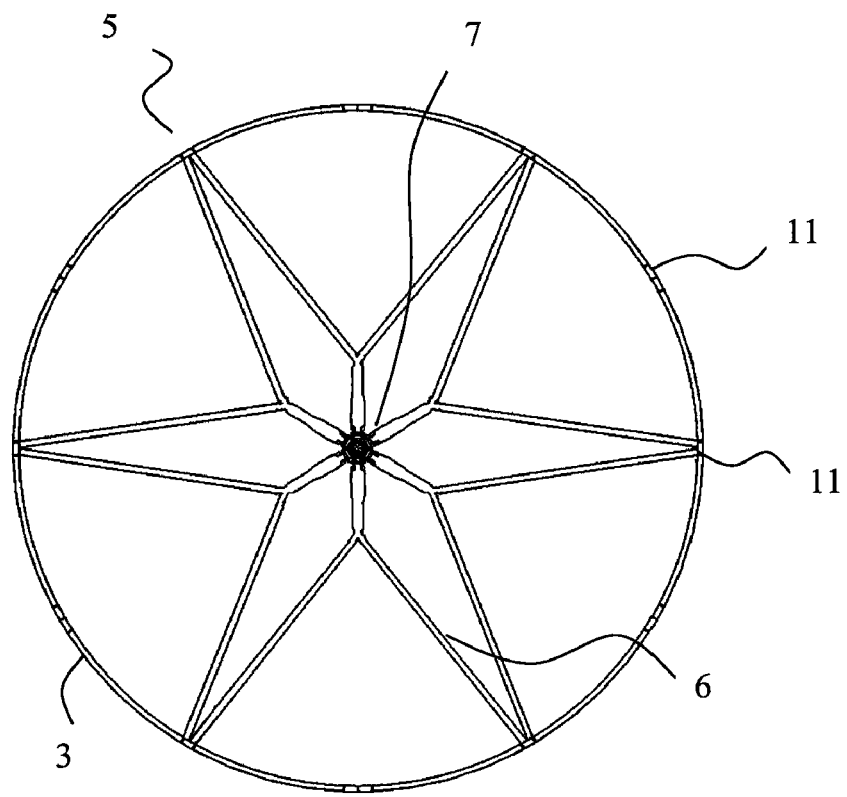
FIG. 7(a) is an end view of the vascular filter of FIG. 1 during manufacture.
Figure 7B:
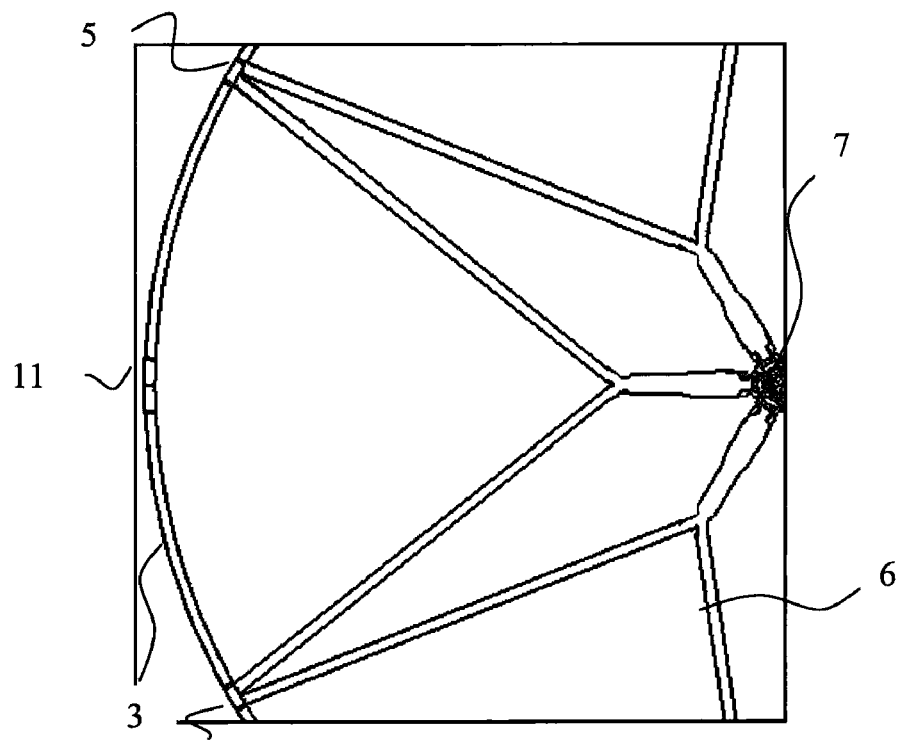
FIG. 7(b) is an enlarged end view of part of the vascular filter of FIG. 7(a) during manufacture.

During manufacture the capture arms 6 are formed into the curved shapes. FIGS. 7(a) and 7(b) illustrate the capture arms 6 before forming into the curved shapes. FIGS. 7(a) and 7(b) illustrate the cut pattern of FIG. 2 expanded without heat setting the capture arms 6.

When the filter 1 is deployed in the inferior vena cava, the apex 7 is substantially in-line with the longitudinal axis extending through the centre of the inferior vena cava, and the filtration cone 8 is located in the region of the centre of the inferior vena cava. When the filter 1 is deployed in the inferior vena cava, the capture arms 6 extend in the direction of blood flow through the inferior vena cava.

The capture arms 6 are movable from the capturing configuration to the open configuration upon elapse of the predetermined period of time. The capture arms 6 are biased towards the open configuration.

The filter 1 comprises a holder member at the distal ends of the capture arms 6 to temporarily hold the capture arms 6 in the capturing configuration until elapse of the predetermined period of time. The holder member engages with each capture arm 6 to hold the capture arms 6 in the capturing configuration. At least part of the holder member is biodegradable and/or bioabsorbable upon elapse of the predetermined period of time. Upon biodegrading/bioabsorbing of the holder member, the capture arms 6 are free to move from the capturing configuration to the open configuration. The capture arms 6 are not biodegradable or bioabsorbable.

The distal end of the distal support hoop 4 is located distally of the capture arms 6 and the apex 7, and the proximal end of the proximal support hoop 3 is located proximally of the capture arms 6.

When the filter 1 is deployed in the inferior vena cava, the support hoops 3, 4 and the support struts 5 exert a force radially outwardly on the internal wall of the inferior vena cava. In this manner the support hoops 3, 4 and the support struts 5 support the capture arms 6 in position relative to the wall of the inferior vena cava 2.

In the capturing configuration the maximum distance between each support strut 5 and a wall of a blood vessel may be less than 4 mm, and preferably is less than 2 mm. In the capturing configuration the concave portion of the curve 14 of the support struts 5 may face radially outwardly (FIG. 4), or alternatively the support struts 5 may be straight, or alternatively the convex portion of the curve 14 of the support struts 5 may face radially outwardly.

As illustrated in FIG. 8, when the filter is deployed externally of a blood vessel, in the open configuration the convex portion of the curve 14 of the support struts 5 faces radially outwardly. In the open configuration the ratio of R1:R2 is in the range of from 1:1 to 1.5:1, where R1 is the distance of each support strut 5 from the central longitudinal axis of the filter 1 at the point along the support strut 5 where this distance is at a maximum, and R2 is the distance of the support strut 5 from the central longitudinal axis of the filter 1 at an end of the support strut 5 where the support strut 5 is connected to either the proximal support hoop 3 or the distal support hoop 4.

In this case the largest radius R1 of the convex portion of the curve 14 is 17 mm, and the radius R2 of the proximal support hoop 3 and the distal support hoop 4 is 15 mm. The barrel shape of the filter 1 reduces any bowing or lift-off of the support struts 5 from the blood vessel wall, increases the contact force of the support hoops 3, 4 with the blood vessel, and improves buckling resistance.

In use the filter 1 is collapsed to the delivery configuration (FIGS. 2 and 3), and at least partially loaded into a delivery catheter. The delivery catheter is advanced through the inferior vena cava until the collapsed filter 1 reaches the desired location in the inferior vena cava. A restraining sheath of the delivery catheter is then moved proximally relative to the filter 1 to fully uncover the filter 1. Due to the biasing nature of the filter 1, the filter 1 moves from the collapsed delivery configuration to the expanded deployed configuration (FIG. 4). In the deployed configuration, the support hoops 3, 4 and the support struts 5 exert a radially outward force on the internal wall of the inferior vena cava to support the capture arms 6 in the desired position in the inferior vena cava.

In the event of thrombus passing through the inferior vena cava towards the heart and the lungs, the thrombus will be captured in the capture region 8 of the filter 1. The thrombus will thus be prevented from passing into the heart and the lungs which could otherwise lead to pulmonary embolism. The captured thrombus will gradually be broken down by the body into smaller size particles which will significantly reduce the risk of embolism.

The holder member temporarily holds the capture arms 6 in the capturing configuration until elapse of the predetermined period of time. Upon elapse of the predetermined period of time the holder member biodegrades/bioabsorbs. This enables the capture arms 6 to move from the capturing configuration to the open configuration (FIG. 8). In the open configuration the filter 1 facilitates unrestricted blood flow. The support hoops 3, 4, the support struts 5 and the capture arms 6 remain in the inferior vena cava.

It will be appreciated that the proximal support hoop 3 and/or the distal support hoop 4 may comprise any suitable number of distal peaks and proximal peaks. For example the proximal support hoop 3 and/or the distal support hoop 4 may comprise eleven distal peaks and eleven proximal peaks, or may comprise ten distal peaks and ten proximal peaks, or may comprise nine distal peaks and nine proximal peaks, or may comprise eight distal peaks and eight proximal peaks, or may comprise seven distal peaks and seven proximal peaks, or may comprise five distal peaks and five proximal peaks, or may comprise four distal peaks and four proximal peaks, or may comprise three distal peaks and three proximal peaks.

Figure 9:
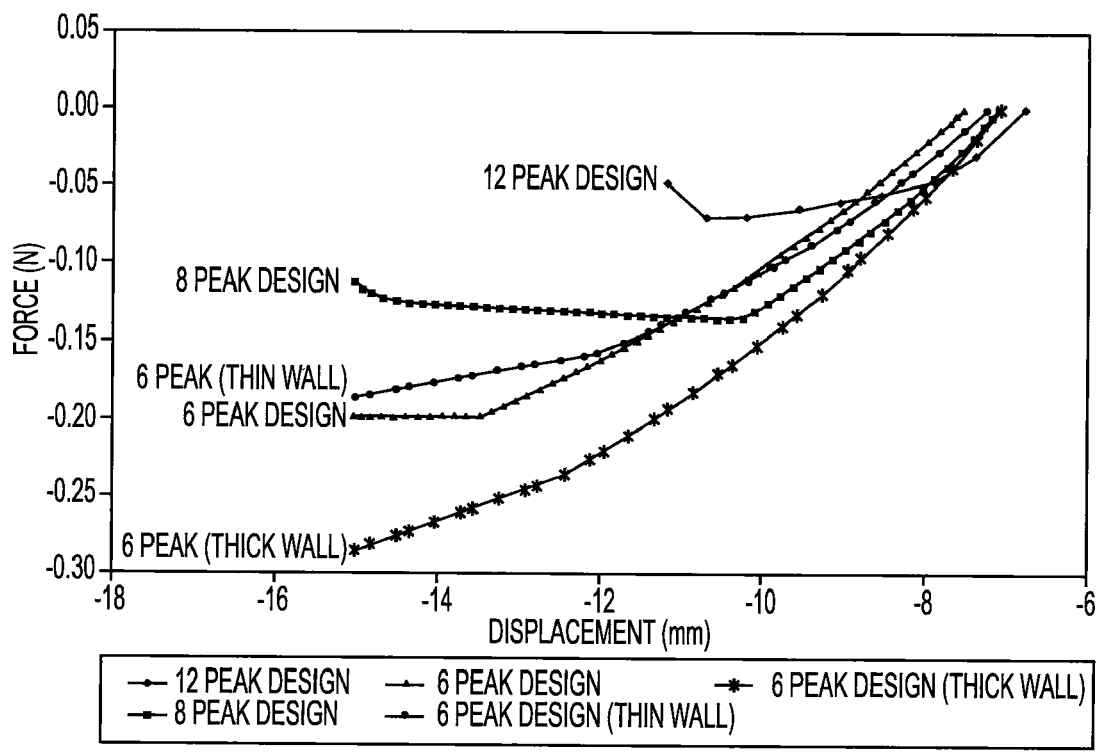
FIG. 9 is a graph of force versus displacement.

FIG. 9 illustrates the buckling behaviour of filters having a different number of peaks. Each filter was placed in a blood vessel having a 16 mm diameter and a crown tip 11 was pulled toward the centre of the blood vessel. The reaction force or force exerted by the filter against this movement is plotted on the graph of FIG. 9. The force and displacement values on the graph are negative as the force is a compressive/pushing force and the crown tip 11 is moving negatively into the centre of the blood vessel.

FIG. 9 illustrates that at the largest displacement the filter having six distal peaks and six proximal peaks exerts a particularly high force against the deformation applied, and thus the filter having six distal peaks and six proximal peaks is highly resistant to buckling.

Figure 10:
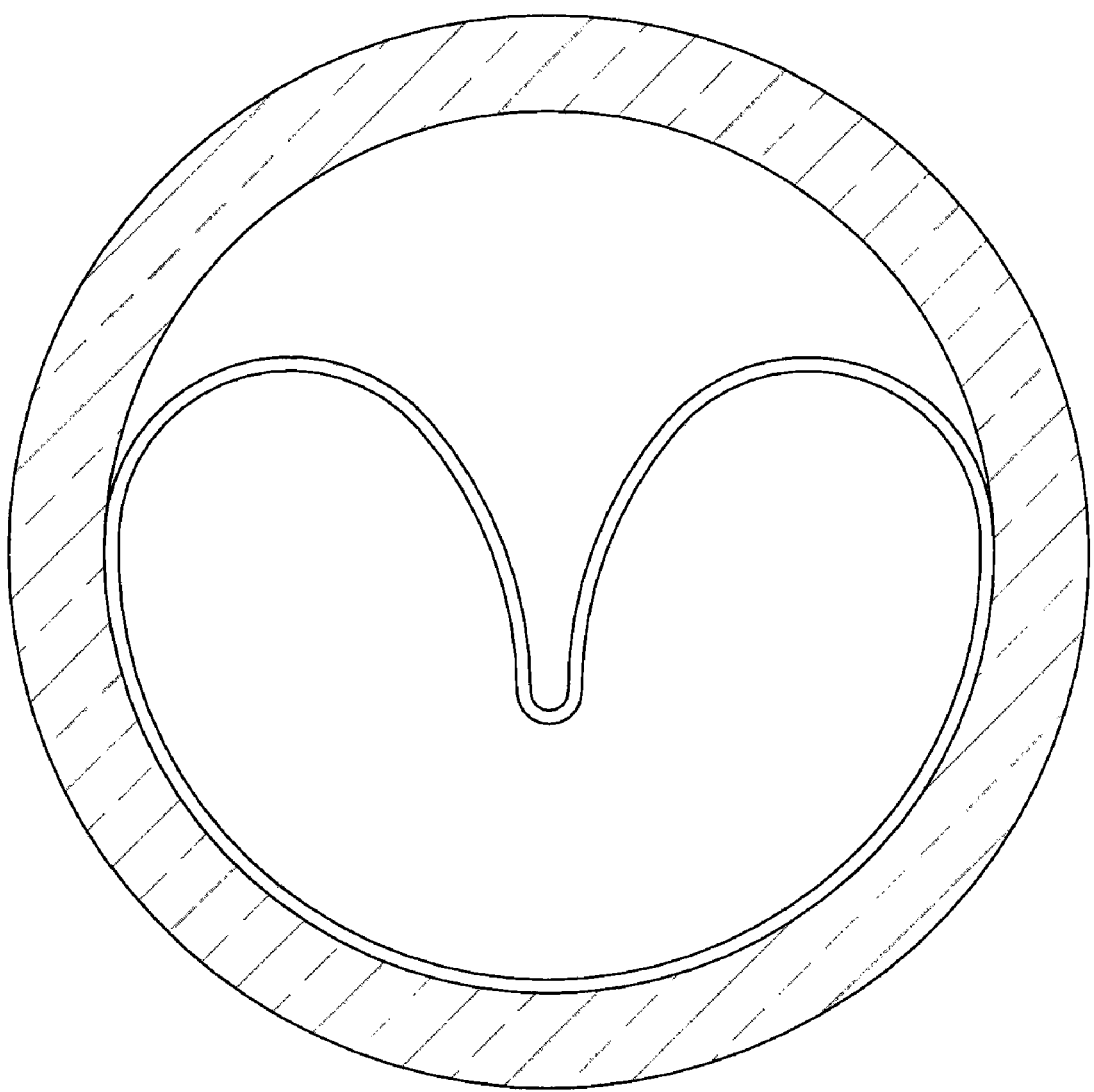
FIG. 10 is an end view illustrating buckling of a vascular filter.

FIG. 10 illustrates buckling of a vascular filter deployed in a blood vessel.

The invention is not limited to the embodiment hereinbefore described, with reference to the accompanying drawings, which may be varied in construction and detail.

The invention claimed is:

1. A vascular filter comprising:
   capture members configured to capture thrombus passing through a blood vessel, the capture members being movable from a capturing configuration to an open configuration, and
   support members for supporting the capture members,
   the support members, in an unconstrained condition, including:
   a proximal hoop extending circumferentially in a wave pattern;

a distal hoop extending circumferentially in a wave pattern; and connecter elements extending from the proximal hoop to the distal hoop, wherein one or more of the connector elements bow toward a longitudinal axis of the filter when the capture members are in the capturing configuration, the one or more connecter elements being convex with respect to the longitudinal axis from the proximal hoop to the distal hoop when the capture members are in the capturing configuration, the one or more connector elements being configured to move outward when the capture members move to the open configuration, the one or more connecter elements being concave with respect to the longitudinal axis from the proximal hoop to the distal hoop when the capture members are in the open configuration.

2. A filter as claimed in claim 1, wherein in the capturing configuration, the capture members are configured to capture thrombus passing through a blood vessel.

3. A filter as claimed in claim 2, wherein in the capturing configuration, the capture members extend towards an apex.

4. A filter as claimed in claim 3, wherein, in the capturing configuration, the capture members curve as they extend towards the apex.

5. A filter as claimed in claim 3, wherein each of the capture members is connected to a distal peak of the wave pattern of the proximal hoop.

6. A filter as claimed in claim 5, wherein a first capture member is connected to a first distal peak of the wave pattern of the proximal hoop, and a second capture member is connected to the first distal peak of the wave pattern of the proximal hoop.

7. A filter as claimed in claim 6, wherein in the capturing configuration, the first capture member extends from the first distal peak of the wave pattern of the proximal hoop towards the apex in a first curve, and the second capture member extends from the first distal peak of the wave pattern of the proximal hoop towards the apex in a second curve, a concave portion of the first curve facing inwardly towards a concave portion of the second curve.

8. A filter as claimed in claim 1, wherein each of the connecter elements connects a peak of the wave pattern of the proximal hoop to a peak of the wave pattern of the distal hoop.

9. A filter as claimed in claim 1, wherein the proximal hoop comprises an enlarged end element at a peak of the wave pattern of the proximal hoop.

10. A filter as claimed in claim 9, wherein in a delivery configuration, a diameter of curvature of the enlarged end element is greater than a distance between adjacent connector elements.

11. A filter as claimed in claim 1, wherein the wave pattern of the distal hoop comprises less than twelve distal peaks.

12. A filter as claimed in claim 11, wherein the wave pattern of the distal hoop comprises less than ten distal peaks.

13. A filter as claimed in claim 12, wherein the wave pattern of the distal hoop comprises less than eight distal peaks.

14. A filter as claimed in claim 1, wherein each of the connecter elements is configured to extend longitudinally along a wall of a blood vessel.

15. A filter as claimed in claim 14, wherein in the capturing configuration, a maximum distance between the connecter elements and the wall of the blood vessel is less than 4 mm.

16. A filter as claimed in claim 15, wherein in the capturing configuration, the maximum distance between the connector elements and the wall of the blood vessel is less than 2 mm.

17. A filter as claimed in claim 1, wherein a radial dimension of the support members is greater than 0.20 mm.

18. A filter as claimed in claim 17, wherein the radial dimension of the support members is greater than 0.25 mm.

19. A filter as claimed in claim 18, wherein the radial dimension of the support members is greater than 0.30 mm.

20. A filter as claimed in claim 1, wherein a width of at least a part of one of the support members is greater than 0.25 mm.

21. A filter as claimed in claim 20, wherein the width of at least a part of one of the support members is greater than 0.30 mm.

22. A filter as claimed in claim 21, wherein the width of at least a part of one of the support members is greater than 0.35 mm.

23. A vascular filter comprising:
capture members configured to capture thrombus passing through a blood vessel, the capture members being movable from a capturing configuration to an open configuration, and support members for supporting the capture members, the support members, in an unconstrained condition, including:

a proximal hoop extending circumferentially;

a distal hoop extending circumferentially; and connecter elements extending from the proximal hoop to the distal hoop, wherein at least one of the connector elements is convex with respect to a longitudinal axis of the vascular filter from the proximal hoop to the distal hoop when the capture members are in the capturing configuration, the connector elements being configured to move outward when the capture members move from the capturing configuration to the open configuration, the connecter elements being concave with respect to the longitudinal axis of the filter from the proximal hoop to the distal hoop when the capture members are in the open configuration.

24. A vascular filter comprising:
capture members configured to capture thrombus passing through a blood vessel, the capture members being movable from a capturing configuration to an open configuration, and support members for supporting the capture members, the support members, in an unconstrained condition, including:

a proximal hoop extending circumferentially;

a distal hoop extending circumferentially; and connecter elements extending from the proximal hoop to the distal hoop, wherein at least one of the connector elements is convex with respect to a longitudinal axis of the vascular filter from the proximal hoop to the distal hoop when the capture members are in the capturing configuration, the connector elements being configured to move outward when the capture members move from the capturing configuration to the open configuration, a portion of the connector elements being configured to be positioned radially outerwardly of the proximal and distal hoops when the capture members are in the open configuration.

* * * * *

UNITED STATES PATENT AND TRADEMARK OFFICE
CERTIFICATE OF CORRECTION

| | | |
|---|---|---|
| PATENT NO. | : 8,057,507 B2 | Page 1 of 1 |
| APPLICATION NO. | : 12/355556 | |
| DATED | : November 15, 2011 | |
| INVENTOR(S) | : Steven Horan, Jacquline O'Gorman and Aidan Goggin | |

It is certified that error appears in the above-identified patent and that said Letters Patent is hereby corrected as shown below:

Claim 24, col. 8, lines 59-60, "outerwardly" should read --outwardly--.

Signed and Sealed this
Sixth Day of March, 2012

David J. Kappos
*Director of the United States Patent and Trademark Office*